(12) United States Patent
Miller et al.

(10) Patent No.: US 7,364,296 B2
(45) Date of Patent: Apr. 29, 2008

(54) METHOD AND APPARATUS FOR IMPROVING BOTH LATERAL AND AXIAL RESOLUTION IN OPHTHALMOSCOPY

(75) Inventors: Donald T. Miller, Bloomington, IN (US); Ravi S. Jonnal, Bloomington, IN (US); Junle Qu, Bloomington, IN (US); Karen E. Thorn, Lower Hutt (NZ)

(73) Assignee: University of Rochester, Rochester, NY (US)

( * ) Notice: Subject to any disclaimer, the term of this patent is extended or adjusted under 35 U.S.C. 154(b) by 258 days.

(21) Appl. No.: 10/517,367

(22) PCT Filed: Jun. 11, 2003

(86) PCT No.: PCT/US03/18511

§ 371 (c)(1),
(2), (4) Date: Aug. 26, 2005

(87) PCT Pub. No.: WO03/105678

PCT Pub. Date: Dec. 24, 2003

(65) Prior Publication Data

US 2006/0058682 A1    Mar. 16, 2006

Related U.S. Application Data

(60) Provisional application No. 60/388,036, filed on Jun. 12, 2002.

(51) Int. Cl.
*A61B 3/14*    (2006.01)
*A61B 3/10*    (2006.01)

(52) U.S. Cl. .......................... 351/206; 351/221

(58) Field of Classification Search ................ 351/205
See application file for complete search history.

(56) References Cited

U.S. PATENT DOCUMENTS 4,579,430 A * 4/1986 Bille ........................... 351/206
4,900,144 A * 2/1990 Kobayashi ................... 351/206

(Continued)

FOREIGN PATENT DOCUMENTS

EP        0 659 383 A2    6/1995

(Continued)

OTHER PUBLICATIONS

M. Wojtkowski et al, "Ultrahigh-resolution, high-speed, Fourier domain optical coherence tomography and methods for dispersion compensation," *Optics Express*, May 31, 2004, vol. 12, No. 11, pp. 2404-2422, © 2004 Optical Society of America.

(Continued)

*Primary Examiner*—Alicia M Harrington
(74) *Attorney, Agent, or Firm*—Blank Rome LLP

(57) ABSTRACT

The invention provides a method of optical imaging comprising providing a sample to be imaged, measuring and correcting aberrations associated with the sample using adaptive optics, and imaging the sample by optical coherence tomography. The method can be used to image the fundus of a human eye to provide diagnostic information about retinal pathologies such as macular degeneration, retinitis pigmentosa, glaucoma, or diabetic retinopathy. The invention further provides an apparatus comprising an adaptive optics subsystem and a two-dimensional optical coherence tomography subsystem.

17 Claims, 9 Drawing Sheets

U.S. PATENT DOCUMENTS

| | | | |
|---|---|---|---|
| 5,465,147 A * | 11/1995 | Swanson | 356/497 |
| 5,537,162 A | 7/1996 | Hellmuth et al. | |
| 5,949,521 A * | 9/1999 | Williams et al. | 351/246 |
| 6,120,461 A * | 9/2000 | Smyth | 600/558 |
| 6,377,349 B1 | 4/2002 | Fercher | |
| 6,588,900 B1 | 7/2003 | Le Gargasson et al. | |
| 6,663,242 B1 * | 12/2003 | Davenport | 351/221 |
| 7,118,216 B2 | 10/2006 | Roorda | |
| 2004/0156016 A1 * | 8/2004 | Kerr et al. | 351/206 |

FOREIGN PATENT DOCUMENTS

| | | |
|---|---|---|
| EP | 0 659 383 A3 | 6/1995 |
| EP | 0 659 383 B1 | 6/1995 |
| WO | WO 99/65431 A1 | 12/1999 |
| WO | WO 00/59368 A1 | 10/2000 |

OTHER PUBLICATIONS

B. Cense et al, "Ultrahight-resolution high-speed retinal imaging using spectral-domain optical coherence tomography," *Optics Express*, May 31, 2004, vol. 12, No. 11, pp. 2435-2447 © Optical Society of America.

B. Hermann et al, "Adaptive-optics ultrahigh-resolution optical coherence tomography," *Optics Letters*, Sep. 15, 2004, vol. 29, No. 18, pp. 2142-2144, © 2004 Optical Society of America.

* cited by examiner

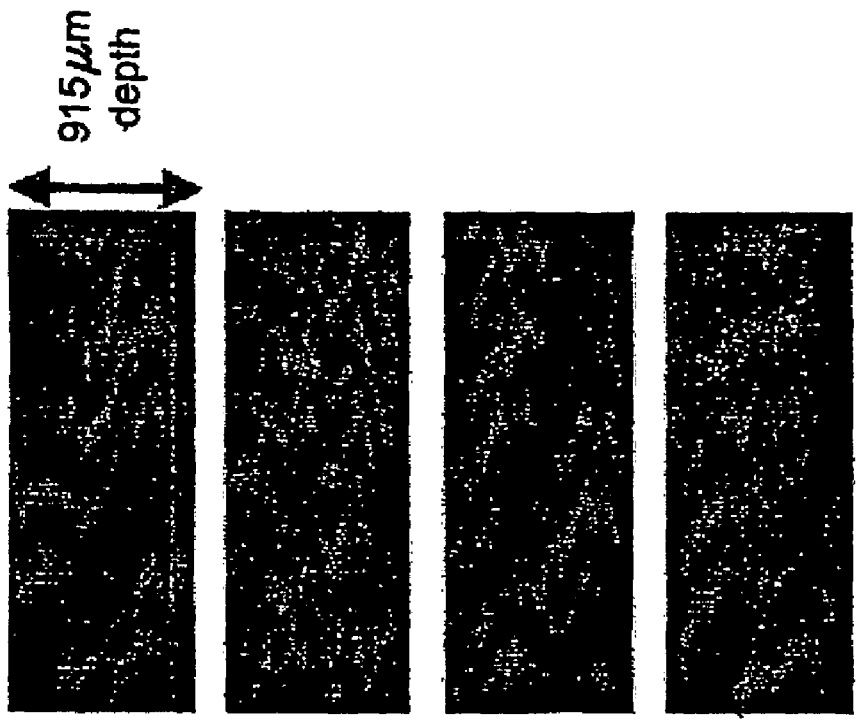
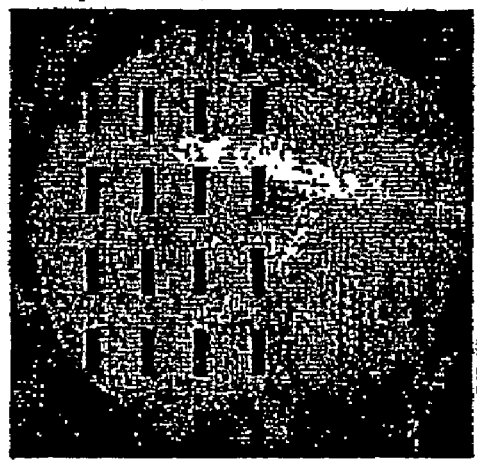

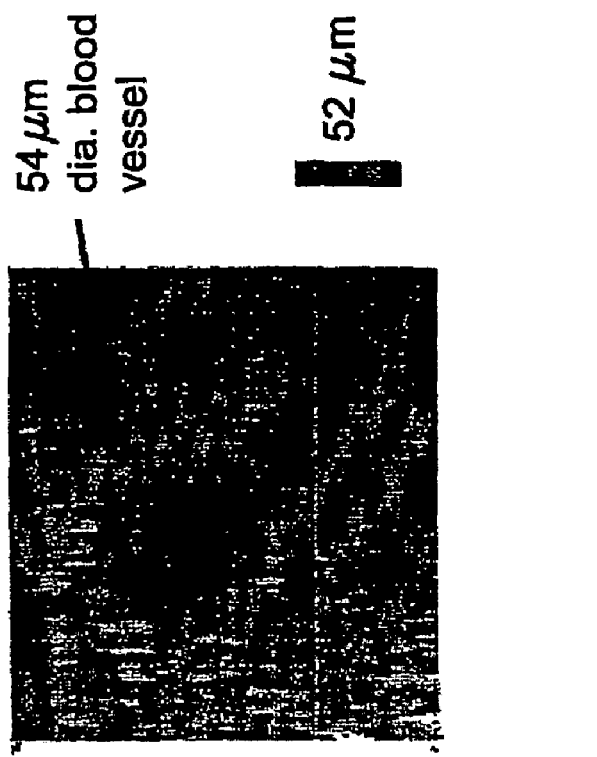
FIG. 6B
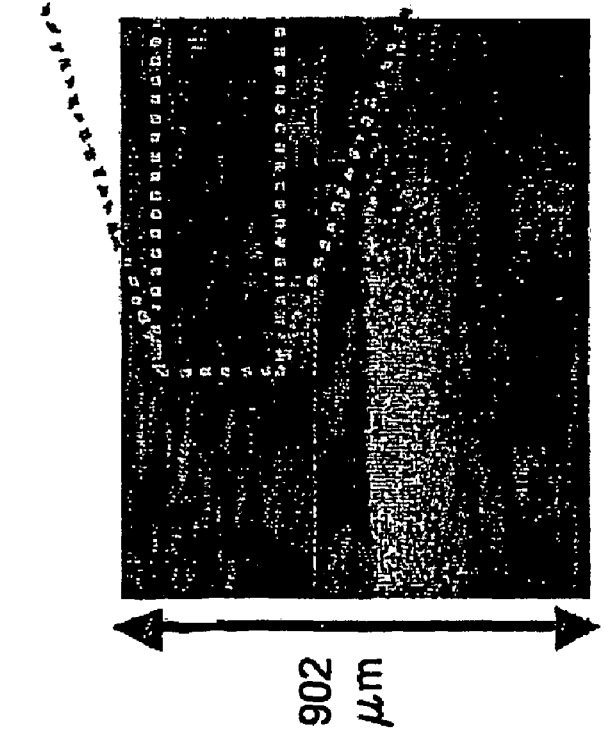
FIG. 6A

Single *en face* (X-Y) reconstructions

15 μm

X-Z slice through
*En face* reconstructions

INL

RPE & choroid

421 μm

METHOD AND APPARATUS FOR IMPROVING BOTH LATERAL AND AXIAL RESOLUTION IN OPHTHALMOSCOPY

CROSS-REFERENCE TO RELATED PATENT APPLICATIONS

This patent application claims the benefit of U.S. Provisional Patent Application No. 60/388,036, filed Jun. 12, 2002, which is incorporated herein by reference.

STATEMENT REGARDING FEDERALLY SPONSORED RESEARCH AND DEVELOPMENT

This invention was made in part with Government support under Grant Number AST-9876783 awarded by the National Science Foundation. The Government may have certain rights in this invention.

FIELD OF THE INVENTION

This invention pertains to an optical imaging method and apparatus. More particularly, the invention relates to the imaging of biological tissue, such as retinal and ocular tissue, preferably at the cellular level, with high quality lateral and axial resolution.

BACKGROUND OF THE INVENTION

The human retina is exceedingly thin, yet its ¹/₁₀₀th of an inch thickness supports a vast microcosm of diverse cells organized in discrete layers, each playing a critical role in the visual process. Cell types present in the retina include ganglion, bipolar, horizontal, amacrine, cone and rod photoreceptor, leukocyte, erythrocyte and retinal pigment epithelial cells. Imaging the retina through the natural pupil of the eye is a critical diagnostic tool for evaluating the health of the eye. Since pathogenesis begins at the cellular level, both the clinician and the researcher best interpret abnormal physiology of the retina when they understand and can visualize these changes in the microscopic realm. For the clinician, when microscopic tissue changes correlate with macroscopic disease, the diagnosis is more precise and timely and the treatment is better informed. Such retinal pathologies include macular degeneration, retinitis pigmentosa, glaucoma, and diabetic retinopathy. Yet despite major advances in retinal cameras, less than 0.2% of human retinal cells have been visualized in vivo and the potential benefit of observing these cells has remained untapped. Retinal microscopy is extremely challenging because (1) optical aberrations primarily in the cornea and crystalline lens substantially blur the retinal image and (2) reflections from cells at many different depths in the thick retina are weak and create a host of superimposed images at the detector.

Adaptive optics (AO), a technique that is well established in the field of astronomy to correct blur induced by atmospheric turbulence, has been applied to measuring and correcting the ocular aberrations of the eye. AO relies on a wavefront sensor that measures the wavefront distortion and sends a signal through a computer processor to a wavefront corrector (e.g. deformable mirror or spatial light modulator), which can be adjusted to correct for the distortion. Some basic principles of AO are described in Tyson, R. K., *Principles of Adaptive Optics*, Academic Press, New York, 1998; and Hardy, J. W., *Adaptive Optics for Astronomical Telescopes*, Oxford University Press, New York, 1998.

Using AO, researchers have been able to routinely observe single cells in the living human retina (see, e.g., Liang et al. *J. Opt. Soc. Am. A*, 14, 2884-2892, 1997). The experiment was conducted using a special camera equipped with AO, which compensated for the most significant ocular aberrations in the subject's eye and provided the eye with unprecedented image quality. A scientific-grade Charge Coupled Device (CCD) array collected—through the compensated optics—short four millisecond images of a flood-illuminated patch of retina. The short exposures were sufficient to adequately freeze retinal motion and preclude blurring. Correction of the ocular aberrations and reduction of retinal motion enabled sharp images of the retina to be collected with enhanced transverse resolution. This increase in transverse resolution was sufficient to enable single cells, such as cone photoreceptors, to be resolved in subjects with normal optics. The AO camera, however, is limited to viewing high contrast retinal structures, namely cone photoreceptors near the fovea and the retinal vasculature. This limitation is likely due to the camera's inherently poor optical sectioning capability (i.e. poor axial resolution) and the relatively large amount of scatter within the thick retina. The use of AO to produce retinal images is disclosed, for example, in U.S. Pat. Nos. 4,838,679, 5,777,719, 5,949,521, 6,095,651, and 6,379,005.

An imaging technique that provides superior axial resolution (i.e., optical sectioning) is coherence gating, also referred to as optical coherence tomography (OCT). OCT is an interference technique in which low temporal coherence light is split into two light beams, which are reflected from a sample object to be imaged and a reference mirror, respectively. The reflected light is then superimposed to generate an interference pattern that is recorded by a detector. The sample image is derived from the interference pattern. Some basic principles of OCT are described in Huang, D. et al., *Science*, 254, 1178-1181, 1991; Fercher, A. F., *J. Biomed. Opt.*, 1, 157-173, 1996; and Bouma, B. E. et al., *Handbook of Optical Coherence Tomography*, 2002. The usefulness of OCT for retinal imaging, however, is limited by significant defocus problems and by blurring that results from the optical aberrations associated with the eye. U.S. Pat. Nos. 5,975,697, 6,095,648, 6,137,585, 6,288,784, 6,293,674, 6,307,634, and 6,325,512, as well as published U.S. Patent Application 2001/0043332 A1, U.S. Patent Application 2001/0000978 A1, and EP 659 383 A2, disclose the use of OCT for imaging the retina.

Despite the availability of the foregoing approaches, there remains a need for an imaging method and apparatus that provides both high transverse resolution and axial resolution in the sample image. The invention provides such a method and apparatus. These and other advantages of the invention, as well as additional inventive features, will be apparent from the description of the invention provided herein.

BRIEF SUMMARY OF THE INVENTION

The invention provides a method and apparatus for optical imaging of tissue by combining the techniques of optical coherence tomography (OCT) and adaptive optics (AO). In one aspect, the invention is directed to a method of optical imaging comprising providing a sample to be imaged, measuring and correcting aberrations associated with the sample using AO, and imaging the sample by OCT. In another aspect, the invention is further directed to an optical imaging system comprising an OCT system that is modified with a wavefront corrector and wavefront sensor for performing AO. In a preferred embodiment, the optical imaging apparatus comprises (a) a point light source for AO, (b) a Shack-Hartmann wavefront sensor, (c) a wavefront corrector, (d) a low temporal coherence superluminescent diode 2D-OCT light source, (e) a beam splitter, (f) a reference mirror, (g) a means of modulating an optical path length of a reference beam, (h) a 2D-OCT CCD detector, (i) a low temporal coherence superluminescent diode 1D-OCT light source, (j) a 1D-OCT detector, and (k) a low coherent flood illumination light source coupled to a multi-mode fiber.

The present invention may be best understood with reference to the following detailed description of the preferred embodiments in conjunction with the accompanying drawings.

BRIEF DESCRIPTION OF THE DRAWINGS

FIG. 5a depicts a low coherent flood-illuminated image of a small patch of in vitro bovine retina obtained by blocking the reference channel of the OCT system.

FIG. 5b depicts four cross-sectional (x-z) slices through a stack of 61 en face (x-y) OCT reconstructions of an in vitro bovine retina.

FIG. 6a depicts a cross-sectional slice through a stack of 200 en face (x-y) coherence gated reconstructions of an in vitro bovine retina.

FIG. 6b depicts a subsection of the x-z slice through a stack of en face (x-y) coherence gated reconstructions of an in vitro bovine retina

DETAILED DESCRIPTION OF THE INVENTION

Figure 1:
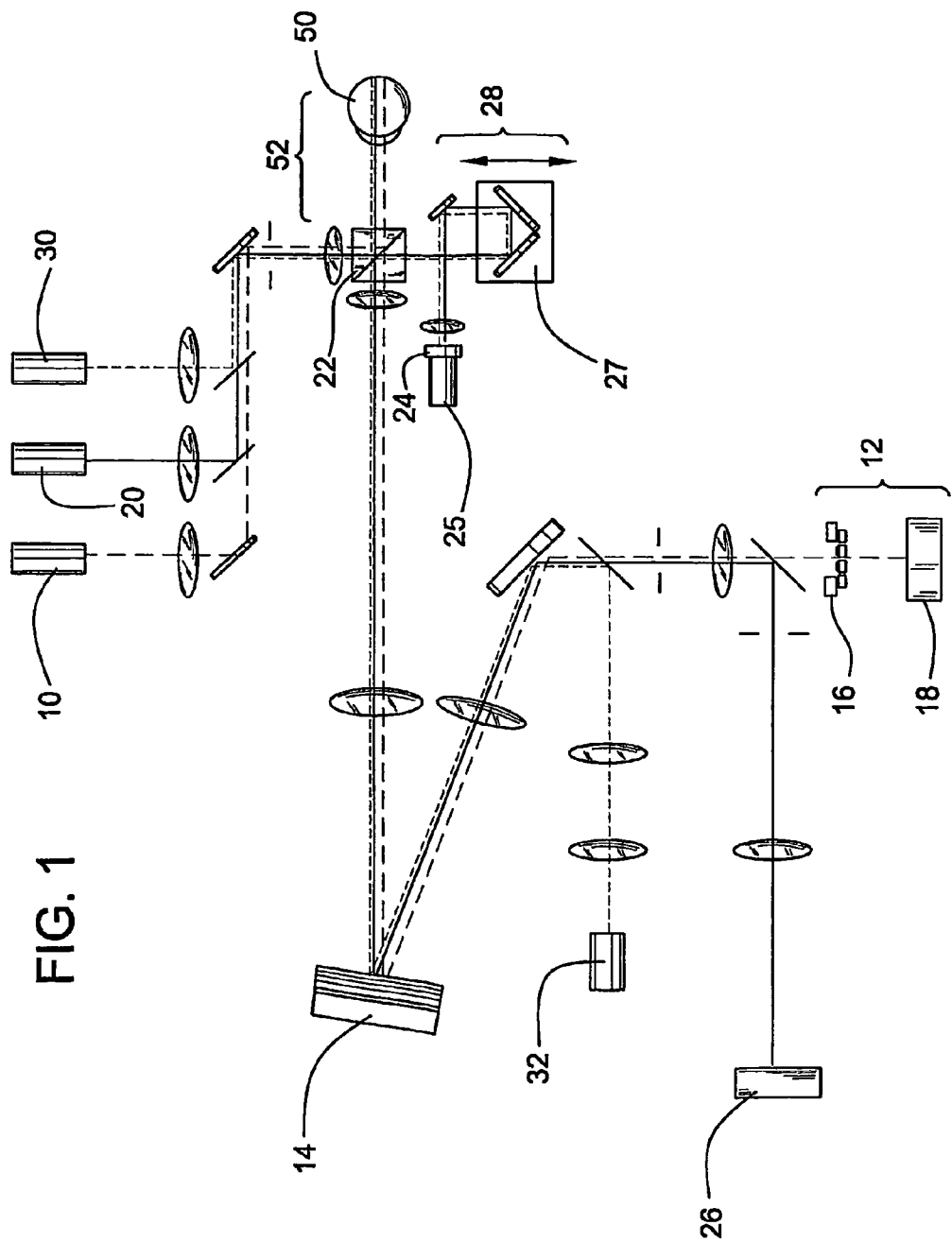
FIG. 1 depicts an AO-OCT apparatus according to a preferred embodiment of the invention.

The present invention is premised, at least in part, on the surprising and unexpected discovery that the resolution benefits afforded by adaptive optics (AO) for viewing high contrast retinal structures can be extended to fainter retinal structures and structures lying further beneath the retinal surface by merging it with an optical coherence tomography (OCT) imaging methodology designed specifically for optical sectioning. Thus, in one aspect, the invention is directed to a method of and apparatus for optical imaging.

The imaging method generally comprises providing a sample to be imaged, measuring and correcting optical aberrations associated with the sample using adaptive optics, and imaging the sample by coherence gating. The aberrations associated with the sample can be determined by measuring the difference between the wavefront reflected from the sample and a reference wavefront (e.g., a planar or spherical reference wavefront). In particular, the aberrations associated with the sample are measured and corrected by (i) illuminating the sample with a point source light beam having a wavefront, (ii) detecting the wavefront of the point source light beam that is reflected from the sample with a wavefront sensor to measure wavefront distortions of the sample, and (iii) adjusting a wavefront corrector so as to compensate for wavefront distortions that are associated with the sample. The sample is imaged by (iv) generating a beam of low temporal coherence light from a light source, (v) splitting the beam of low temporal coherence light to create a sample light beam and a reference light beam, each having an optical path length corresponding to a coherence gate position at a desired region of the sample to be imaged, (vi) illuminating the sample with the sample light beam, (vii) illuminating a reference mirror with the reference light beam, (viii) superimposing the reflected sample light beam and reflected reference light beam to obtain an interference pattern corresponding to the coherence gate position, (ix) recording the interference pattern using a detector (referred to herein as a 2D-OCT detector), and (x) generating a two-dimensional (2D) image of the sample from the interference pattern. The 2-D image can be in any suitable form, including an intensity image, a phase image, a Doppler image, and a polarization image. Optionally, the method further comprises (xi) changing the optical path length to generate a series of coherence gate positions within the sample, (xii) recording a series of interference patterns and generating a series of corresponding 2D images from the interference patterns, and (xiii) constructing a three-dimensional image of the sample from the two-dimensional images.

Typically the AO and OCT steps, respectively, are carried out in the order recited above. The AO steps (i.e., steps i-iii) desirably are carried out before the interference pattern is recorded by the 2D-OCT detector (i.e., step ix). The AO process is an iterative process. Accordingly, steps (i)-(iii) are repeated in a closed loop until the proper correction is achieved. Typically, the AO steps are performed prior to the OCT method steps. Preferably, the AO steps are performed both prior to and concurrent with the OCT method steps.

The imaging method can be used to image any suitable sample, and is particularly well suited for use in imaging samples that have a large number of aberrations associated therewith. Typically, the sample is biological tissue, for example, an eye (e.g., retinal tissue, fundus tissue, a cornea, or crystalline lens of an eye) or skin tissue (e.g., of a mammal such as a human). The method of the invention can also be used for imaging teeth. In preferred embodiments, the sample to be imaged is a retina of an eye. The aberrations associated with the sample can originate from any part of the sample. For example, when imaging a retina of an eye, the aberrations originate in the optics of the eye (e.g., the cornea and crystalline lens of the eye). When the sample is a skin tissue, tooth, or other bodily tissue where a refractive index mismatch exists between sample and surround, typically the aberrations originate from the surface of the sample due to the marked change in refractive index. Aberrations can also result from a change in the thickness of the sample.

In another aspect, the invention is further directed to an imaging apparatus comprising a coherence gating system that is modified with a wavefront corrector and wavefront sensor for performing adaptive optics. The optical imaging apparatus typically is based on a Michelson interferometer design. In particular, the optical imaging apparatus comprises an AO subsystem and a 2D-OCT subsystem.

As seen in FIG. 1, the AO subsystem comprises (a) a point light source 10, (b) a wavefront sensor 12, and (c) a wavefront corrector 14. In a preferred embodiment, wavefront sensor 12 is a Shack-Hartmann wavefront sensor consisting of a two-dimensional array of lenslets 16 and a detector 18. The 2D-OCT subsystem comprises (d) a low temporal coherence 2D-OCT light source 20, (e) a beam splitter 22, (f) a reference mirror 24, (g) a means of modulating an optical path length of a reference beam, and (h) a 2D-OCT detector 26. The 2D-OCT subsystem can further comprise an electro-mechanical device 25 and a translation stage 27 in reference channel 28 with reference mirror 24. In some embodiments, the AO-OCT system further comprises a 1D-OCT low temporal light source 30 and a 1D-OCT detector 32.

A point source light beam of the AO subsystem can be generated from any suitable point light source 10. It will be readily understood by one of ordinary skill in the art that the point light source can be any suitable light source having a substantially focused light beam and a radially symmetric profile. Typically, the point source light beam is generated from a laser diode or a superluminescent diode (SLD). The point source light beam can have any suitable wavelength. For example the point source light beam can be visible or near infrared light. Preferably, the point source light beam has a wavelength in the infrared region (e.g., about 0.7 to about 1.2 microns, or about 0.75 to about 0.95 microns). In one embodiment, the point source light beam has a wavelength of about 0.788 microns. The point source light beam is focused onto the sample, which reflects at least a portion of the light.

The point source light beam that is reflected from sample 50 is collected by wavefront sensor 12, which measures the amount of wavefront distortion that results from aberrations associated with sample 50. Wavefront sensor 12 can be in any suitable form, many of which are commonly known in the art. Wavefront sensor 12 can be based on the Shack-Hartmann technique to measure the gradient of a wavefront, or the wavefront sensor can be a curvature wavefront sensor, shearing interferometer, point diffraction interferometer, phase shifting interferometer, or pyramid wavefront sensor. Wavefront sensor 12 typically is a Shack-Hartmann wavefront sensor consisting of a two-dimensional array of lenslets 16 having a short focal length and detector 18 positioned at the back of the focal plane. Typically, detector 18 of wavefront sensor 12 is a CCD camera. The Shack-Hartmann wavefront sensor can have any suitable number of lenslets, focal length, and pixel spacing. Preferably, wavefront sensor 12 is in the form of a Shack-Hartmann wavefront sensor employing a 17×17 lenslet array.

The information collected by the wavefront sensor is processed by a computer algorithm that measures the amount of wavefront distortion caused by the aberrations of the sample. Such a computer algorithm is within the skill of the ordinary artisan. The computer then provides an output signal to wavefront corrector 14 providing the amount of correction needed to compensate for the wavefront distortion. Following an iterative procedure, wavefront corrector 14 ultimately imparts a shape onto the wavefront that is identical, but opposite in sign to the wavefront distortion measured at the outset. These AO iterations are carried out in a closed loop system, which preferably can operate at up to about 22 wavefront measurements and corrections per second. The correction is sufficient to flatten the distorted wavefront into a plane wave thereby improving the image quality. As described above, at least one cycle of correction should take place prior to 2D-OCT image detection.

Wavefront corrector 14 can be in any suitable form, many of which are commonly known in the art. In some embodiments, wavefront corrector 14 is a deformable mirror that comprises a flexible mirror material bound to an array of actuators. The actuators function to adjust the shape of the mirror to within +/−2 microns or more (e.g., within +/−5 microns or more). Such actuators typically are piezo-electric materials, for example, PZT (lead zirconate titanate), PLZT (lead lanthanide zirconate titanate), PFN (lead iron niobate), PMW (lead magnesium tunstate), PNN (lead nickel niobate), PMN (lead magnesium niobate), or doped PMN materials. Wavefront corrector 14 also can be a bimorph mirror containing two piezoelectric materials that are bonded together and oppositely polarized, a membrane mirror such as a continuous membrane deformable mirror (CMDM), a liquid crystal spatial light modulator (LC-SLM), or a micro-opto-electro-mechanical system (MOEMS, i.e., a micro-mirror). Typically, the wavefront corrector consists of a flexible glass material that is coated with aluminum and contains a plurality of piezo-electric actuators (e.g., about 20 or more) adhered to the backside. LC-SLMs and MOEMS in particular have the potential to be small and inexpensive. In a preferred embodiment, wavefront corrector 14 has a small area thus requiring less system magnification of the aberration source in the sample (e.g. cornea and crystalline lens in the eye).

Low temporal coherence 2D-OCT light source 20 can be any suitable light source capable of providing light of sufficient intensity at a wavelength that can be reflected by the sample being imaged. The low temporal coherence light has a broad spectral width that defines a short coherence length. The coherence length refers to the propagation distance over which the light beam will coherently interfere with itself thereby generating an interference pattern. Light having a long coherence length generates at detector 26 a superposition of many interference patterns that originate from light reflected over a broad depth in the sample. The depth over which this interference occurs is roughly equal to the coherence length. Thus an increase in the coherence length results in a decrease in axial resolution. Preferably, the light has a coherence length that is sufficient to provide axial resolution of the sample image on the order of about 20 microns or less (e.g., about 10 microns or less). More preferably, the light source provides axial resolution on the order of about 5 microns or less (e.g., about 2 microns or less). Suitable light sources that can provide light with a short coherence length include, for example, white light sources (e.g., halogen sources, arc lamps, or flashlamps), semiconductor sources (e.g., SLD, light emitting diodes (LED), doped fiber sources, multiple quantum well semiconductor optical amplifiers such as AFC Technologies Inc. BBS 1310-TS) or solid state lasers (e.g., femtosecond lasers such as FemtoLasers FemtoSource OCT-FC, Imra America Femtolite, or Menlo Systems TB-1550). Typically, the low temporal coherence light source is a SLD.

The type of low temporal coherence 2D-OCT light source 20 selected will depend in part on the application. In some embodiments, low temporal coherence 2D-OCT light source 20 is a flood illumination light source, which is capable of illuminating a large area of the sample. The flood illumination light source illuminates the sample en face (x-y). In other embodiments, low temporal coherence 2D-OCT light source 20 is a scanning point source, in which only a small area of the sample is illuminated at any single point in time. The scanning point source can scan axially (z) and laterally (x or y) through the sample (referred to as tomographic scanning) or across both the x and y lateral directions of the sample (referred to as en face scanning). Point scanning sources typically acquire images relatively slowly, thereby increasing the chances for eye motion to degrade the image (e.g image warping where sections of the image are misregistered relative to each other). Using a flood illumination light source allows all of the reflected light to be collected at once thereby reducing degradation of the image by warping and blurring.

The wavelength selected for low temporal coherence 2D-OCT light source 20 will depend on the identity of the sample being imaged. Typically, the low temporal coherence light will have a wavelength of about 0.4 microns or greater. The low temporal coherence light source desirably will have a wavelength of about 2 microns or less (e.g., about 1.6 microns or less, or about 1.2 microns or less). When the sample to be imaged is a retina of an eye, the low temporal coherent light preferably has a wavelength that can be reflected by the retina, typically, about 0.4 to about 1.2 microns (e.g., about 0.5 to about 1 microns). A wavelength of about 1.2 microns or higher typically is absorbed by the ocular media and a wavelength of about 0.4 microns or less may be damaging to the eye. In a preferred embodiment, the low temporal coherence light source is a superluminescent diode having a wavelength of about 0.5 microns to about 0.95 microns (e.g., about 675 nm, about 830 nm, or about 590 nm).

The low temporal coherence light from light source 20 is directed at beam splitter 22, which acts as a partially reflecting mirror such that part of the incoming light is reflected and part passes through unchanged. Beam splitter 22 can be in any suitable form, many of which are commonly known in the art. Typically, the portion of the light that passes through is directed at reference mirror 24 (i.e., through reference channel 28) and the portion of light that is reflected is directed at sample 50 (i.e., through sample channel 52).

The coherence gate position is the axial position in the sample at which the optical path length (OPL) of the sample beam is equal to the OPL of the reference beam (e.g., of the reference channel). During OCT, the OPL of the reference beam is modulated to change the coherence gate of the sample beam. The means of modulating the OPL of the reference beam can be any suitable means. Typically, the optical path length of the reference beam is modulated by moving reference mirror 24 to different positions by an electromechanical device 25, for example a galvanometer or a piezoelectric translator such as those sold by Polytec PI (Auburn, Mass.), or through the use of a fiber-based or bulk electro-optics phase modulator that retards or advances the wavefront of the reference light. Reference channel 28 can further comprise a translation stage 27 such as a voice coil stage, galvanometer or similar device, which is capable of changing the OPL of the reference channel over a greater range than that of the electromechanical device 25. Optionally, the electromechanical and electro-optical devices (25 and 27) can be inserted upstream of the reference channel in what is known as a pre-interferometer. When a flood illumination 2D-OCT light source is used, typically reference mirror 24 is moved in discrete or ramped steps (e.g., about 2 to 8 discrete or ramped steps, or preferably about 4 or 5 discrete or ramped steps) and an interference pattern is recorded for each of the reference mirror positions. Preferably, the number of discrete reference mirror positions is high (e.g., about 4 or more) but the number is bounded by the timeframe of eye movement. In this respect, a greater number of interference patterns gives rise to a higher sensitivity that enables detection of weaker sample reflections.

However, the eye is subject to both transverse and axial movement over time; so the number of positions is a trade-off between motion artifacts (e.g. image blur and inter-image registration errors) and signal to noise. When point source scanning is used, the mirror can be moved rapidly, creating a variety of different path lengths such that a Doppler effect occurs between the reference and sample light, thereby generating a beat frequency (i.e., the absolute value of the difference in the frequency of two waves). The beat frequency can be detected by a photodiode and provides a greater amount of information about the sample. Thus, the ability to collect a beat frequency results in improved image sensitivity and tolerance to sample motion. Any suitable electromechanical or electro-optical device can generate the beat frequency. For example, a Fourier-domain rapid scanning delay line, optical fibers that are stretched, or fiber-based or bulk electro-optics phase modulator can be used. This technique is commonly known as heterodyning.-Heterodyning can also be used with flood illumination although such a design could require the use of a different detector, such as an active pixel array, instead of a CCD array.

Detector 26 (the 2D-OCT detector) collects the light that is reflected from sample 50 and reference mirror 24. Detector 26 is referred to as the 2D-OCT detector so as to distinguish that detector 26 is part of the 2D-OCT subsystem. However, the 2D-OCT detector 26 is not limited to 2D detectors. Detector 26 can be in any suitable form, including both 1D and 2D detectors. For example, detector 26 can be a CCD array camera, an intensified CCD array camera, a Complementary Metal-Oxide Semiconductor (CMOS) array camera, a photodiode, a photodiode array, or an active pixel array (e.g., a photodiode array with electronics that perform heterodyned detection and demodulation by means of mixing and/or combined filtering and rectifying for recoveringsample phase and intensity, and beat frequency information). Such a photodiode array or active pixel array can be 1D or 2D. When light source 20 is a flood illumination light source, detector 26 preferably is a CCD array or an active pixel array. When light source 20 is a scanning point light source, detector 26 preferably is a photodiode or a photodiode array.

Wavefront sensor 12 and wavefront corrector 14 of the AO subsystem can be placed in any suitable position within the OCT subsystem provided that wavefront corrector 14 is upstream of 2D-OCT detector 26. For example, wavefront corrector 14 can be placed in either sample channel 52 (i.e., the channel through which the beam of light that impinges the sample travels) or the 2D-OCT detector channel (i.e., the channel through which the reflected beams of light travel upon approach to the 2D-OCT detector). Preferably, wavefront corrector 14 is placed in sample channel 52. The placement of wavefront corrector 14 within the AO-OCT setup depends, in part, on the size of wavefront corrector 14. Since larger wavefront correctors require a longer path length, it often is preferable to place them in the detector channel. However, when wavefront corrector 14 is placed in the detector channel, the reflected light beam from reference mirror 24 may be forced to unnecessarily pass through wavefront corrector 14, thus resulting in degradation of the reference beam. The extent of degradation can be diminished by focusing the reference light beam onto a small area of wavefront corrector 14.

Wavefront sensor 12 typically is placed downstream from wavefront corrector 14 as shown in FIG. 1. As discussed above, wavefront sensor 12 detects the reflected point source light from sample 50 and determines the amount of correction required. Because the reflected light beam from reference mirror 24 enters the same channel as the reflected point source beam from sample 50, efforts must be made to keep the reflected reference beam from entering wavefront sensor 12 and interfering with the AO diagnostic. This problem can be solved by, for example, (a) focusing the reflected reference beam onto a small part of wavefront sensor 12, which can then be blocked by an opaque target, or if of sufficiently weak intensity, can be ignored in the raw wavefront sensor measurement, (b) polarizing the light from point light source 10 such that it is orthogonal to a linear polarizer placed in reference channel 28, (c) placing a spectral filter in reference channel 28 that selectively filters out the wavelength of the light from point light source 10, or (d) directing point light source 10 such that it does not reflect from reference mirror 24 in reference channel 28.

Desirably, the AO and OCT methods described above are used in conjunction with a 1D-OCT axial scanning method. The distance between the patient's retina and the retina camera varies with involuntary head and eye movements, fundus pulsations, and drifts and microfluctuations in accommodation, which alter the OPL of the eye. Accurate positioning of the coherence gate in the retina requires tracking and compensating for these retina movements relative to the camera. The 1D-OCT technique can be used to track and compensate for these random changes in physical distance between the sample and the optical imaging apparatus (i.e., axial motion of the sample). The 1D-OCT axial scanning method comprises (i) generating a beam of low temporal coherence 1D-OCT light from a light source 30, (ii) splitting the beam of low temporal coherence 1D-OCT light to create a 1D-OCT sample light beam and a 1D-OCT reference light beam, each having an optical path length corresponding to a coherence gate position at a desired region of sample 50 to be imaged, (iii) illuminating sample 50 with the 1D-OCT sample light beam, (iv) illuminating reference mirror 24 with the 1D-OCT reference light beam, (v) superimposing the reflected sample light beam and reflected reference light beam to obtain an interference pattern corresponding to the coherence gate position, (vi) recording a series of interference patterns corresponding to a series of coherence gate positions using 1D-OCT detector 32, (vii) determining a change in axial position of sample 50 by analyzing the interference patterns recorded by 1D-OCT detector 32, and (viii) adjusting the optical path length of the reference light beam (e.g., using voice coil stage 27) so as to axially move the coherence gate position of the sample light beam thereby compensating for the measured axial motion of sample 50.

The 1D-OCT method of tracking and compensating for axial motion of the sample desirably is completed prior to step (ix) of the 2D-OCT method. Preferably, the method of tracking and compensating for axial motion is carried out both prior to and concurrent with steps (iv)-(ix) of the 2D-OCT method. When 1D-OCT is used in combination with both AO and 2D-OCT as described above, typically the 1D-OCT method is carried out after the AO method steps and before the 2D-OCT steps. When the sample is an eye, typically the change in axial position of the sample is determined by analyzing a portion of the reflected 1D-OCT light from the sample, which corresponds to a particularly reflective region of the eye. Such reflective regions include the choroid layer, the RPE layer, and the front of the retina.

In this embodiment, the optical imaging apparatus further comprises a 1D-OCT axial scan subsystem comprising (i) low temporal coherence light source 30 and (j) 1D-OCT detector 32 as shown in FIG. 1. Low temporal coherent 1D-OCT light source 30 can be any suitable light source capable of providing light of sufficient intensity at a wavelength that can be reflected by the sample being imaged, as described above for low temporal coherence 2D-OCT light source 20. Suitable light sources that can provide light with a short coherence length include, for example, white light sources (e.g., halogen sources, arc lamps, or flashlamps), semiconductor sources (e.g., SLD, light emitting diodes (LED), doped fiber sources, multiple quantum well semiconductor optical amplifiers such as AFC Technologies Inc. BBS 1310-TS) or solid state lasers (e.g., femtosecond lasers such as FemtoLasers FemtoSource OCT-FC, Imra America Femtolite, or Menlo Systems TB-1550). Like 2D-OCT light source 20, the wavelength selected for 1D-OCT low temporal coherence light source 30 will depend on the identity of sample 50 being imaged. Typically, the low temporal coherent 1D-OCT light source will have a wavelength of about 0.4 microns or greater. The low temporal coherent 1D-OCT light source desirably will have a wavelength of about 2 microns or less (e.g., about 1.9 microns or less). Preferably, light source 30 is a SLD and the low temporal coherence light has a wavelength of about 0.5 microns to about 1.6 microns (e.g., about 856 nm). 1D-OCT detector 32 can be any suitable detector, for example a photodiode. The use of the 1D-OCT subsystem can be avoided if the coherence gating is sufficiently rapid such that an operator of the optical imaging apparatus can make adjustments in real time.

Wavefront corrector 14 optionally can be used to create the coherence gating. For example, instead of moving reference mirror 24 as described above, the reference beam can be focused onto a small portion of wavefront corrector 14 and an individual piezo-electric translator on the deformable mirror, or active cell element in the case of a LC-SLM, can be used to alter the OPL of the reference beam. In some embodiments, wavefront corrector 14 can be used to either enhance the coherence-gated image or to extract additional data from the coherence gated image. For example, wavefront corrector 14 can be used to reduce speckling in the sample image without sacrificing the image data that is encoded in the speckle.

To assist in focusing the coherence gate of the 2D-OCT subsystem in the sample, the AO-OCT method can further comprise a low coherent 2D flood illumination imaging method. The low coherent flood illumination method comprises the steps of (i) illuminating the sample with a low coherent flood illumination light source to focus on a region of the sample, (ii) detecting the low coherent flood illumination light that is reflected from the sample with a low coherent flood illumination light detector, and (iii) optionally adjusting the focus within the sample to image at a plurality of depths in the sample. The low coherent 2D flood illumination method can be used in combination with the AO, 2D-OCT, and optional 1D-OCT methods described above. Typically, the 2D-flood illumination method is used in combination with the AO, 2D-OCT, and 1D-OCT methods. In this embodiment, the AO steps typically are carried out first, followed by the low coherent 2-D flood illumination, 1D-OCT, and 2D-OCT steps. During the low coherent 2-D flood illumination steps, the reference channel of the 2D-OCT subsystem typically is blocked to prevent interference and other degradation of the recorded image.

Figure 2:
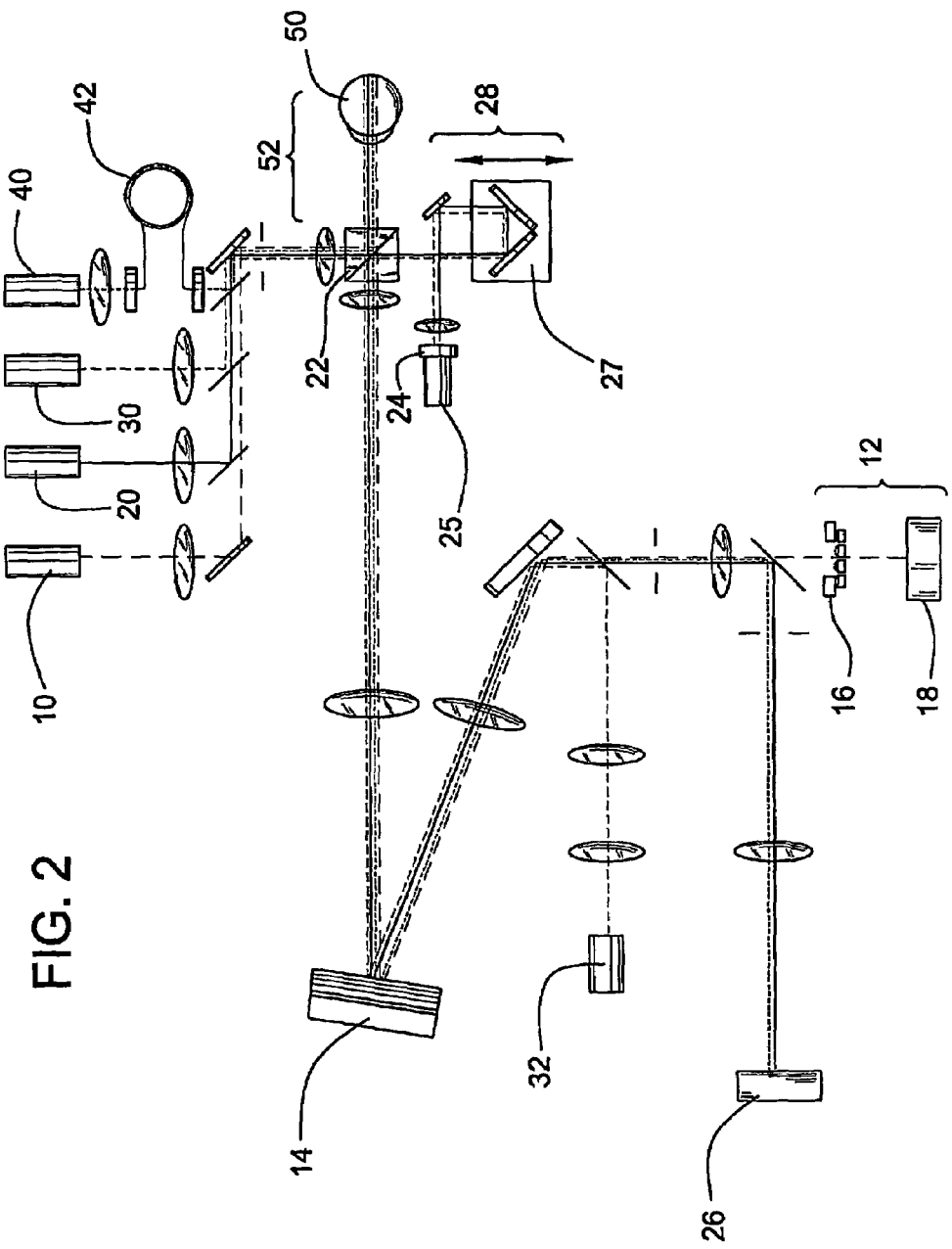
FIG. 2 depicts an AO-OCT apparatus according to a preferred embodiment of the invention.

As shown in FIG. 2, the imaging apparatus can further comprise a low coherence 2-D flood illumination subsystem comprising a low coherent flood illumination light source 40 that flood-illuminates substantially the same or nearby region of sample 50 that is illuminated by low temporal coherent 2D-OCT light source 20. Low coherent flood illumination light source 40 can be any suitable light source including low temporal coherent light sources as described above for the 2D-OCT and 1D-OCT methods, as well as low spatial coherent light sources. The low coherent flood illumination light source can have low temporal coherence, low spatial coherence, or both low temporal and low spatial coherence. Typically, light source 40 has both low temporal and low spatial coherence. The low coherent flood illumination light source can be selected from the group consisting of laser diodes, ultrafast lasers (e.g., femtosecond lasers), mode-locked solid state lasers, dye lasers, SLDs, and LEDs. When low coherent flood illumination light source 40 is a laser diode, ultrafast laser, dye laser, or SLD, light source 40 desirably is coupled to a multi-mode fiber 42. Preferably, light source 40 is a SLD coupled to a multi-mode fiber 42. Multi-mode fiber 42 can propagate any suitable number of modes, for example the multi-mode fiber can propagate 2 or more modes, preferably 100 more, more preferably 500 or more, even more preferably, 1,000 or more, still more preferably, 5,000 or more. One suitable multi-mode fiber is a 5,000-mode fiber having a diameter of about 100 microns and a length of about 25 m. The wavelength of low coherent flood illumination light source 40 can be any suitable wavelength and desirably is similar to the wavelength of low temporal coherence light source 20 used for the 2D-OCT.

Typically, incoherent flood illumination light source 40 is a separate light source, although in some embodiments low temporal coherence 2D-OCT light source 20 is used as low coherent flood illumination light source 40. In these embodiments, the 2D-OCT subsystem further comprises a movable mirror, which can be adjusted such that light from 2D-OCT low temporal coherence light source 20 is either directed into beam splitter 22 (and sample channel 52) or into multi-mode fiber 42 from which it then exits into beamsplitter 22 (and sample channel 52).

Desirably the AO, low coherence 2D flood illumination, and 1D-OCT methods are continued during the 2D-OCT image detection steps. However, the low coherence 2D-flood illumination method can only be carried out during 2D-OCT if the flood illumination light is blocked in some way from entering reference channel 28. For example, the flood illumination light (a) can be polarized such that it is orthogonal to a linear polarizer placed in reference channel 28, (b) can be selected to have a different wavelength such that it can be filtered out using a spectral filter, or (c) the spatial location of the low coherent flood illumination light can be directed such that it does not reflect off reference mirror 24.

Figure 3:
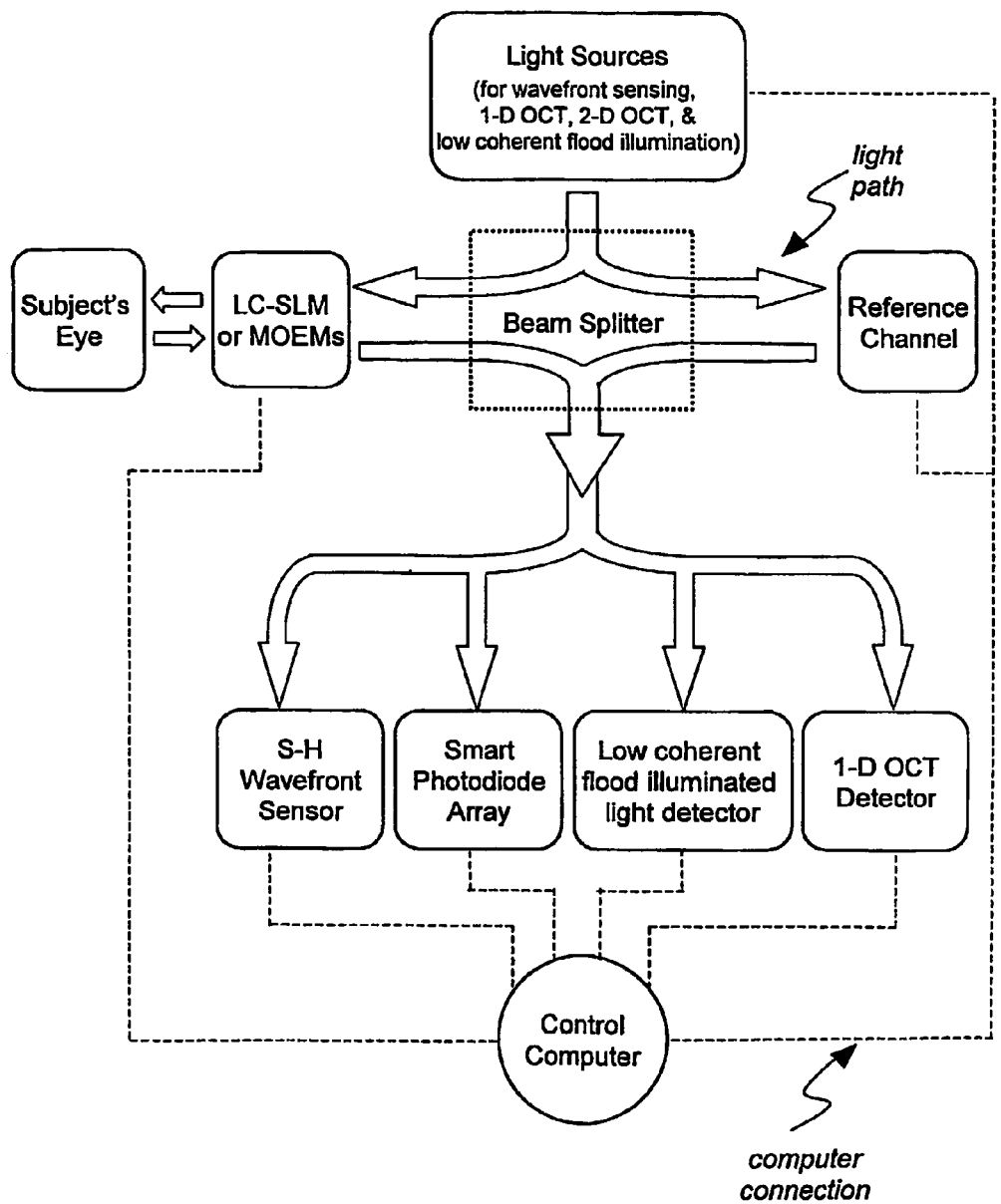
FIG. 3 depicts a flowchart representing a flood illumination AO-OCT apparatus according to a preferred embodiment of the invention.

In some preferred embodiments, the AO-OCT apparatus is a flood-illuminated camera as represented in FIG. 3, wherein wavefront sensor 12 is a Shack-Hartmann (S-H) wavefront sensor, wavefront corrector 14 is a LC-SLM or MOEMs, 2D-OCT detector 26 is an active pixel array (e.g., smart photodiode array), and reference channel 28 consists of an electro-optics phase modulator for heterodyning, a dispersion compensator, and a voice coil stage to position the coherence gate in the retina. The apparatus of this embodiment also comprises a 1D-OCT axial scanning subsystem and low coherent flood illumination subsystem as described above.

Figure 4:
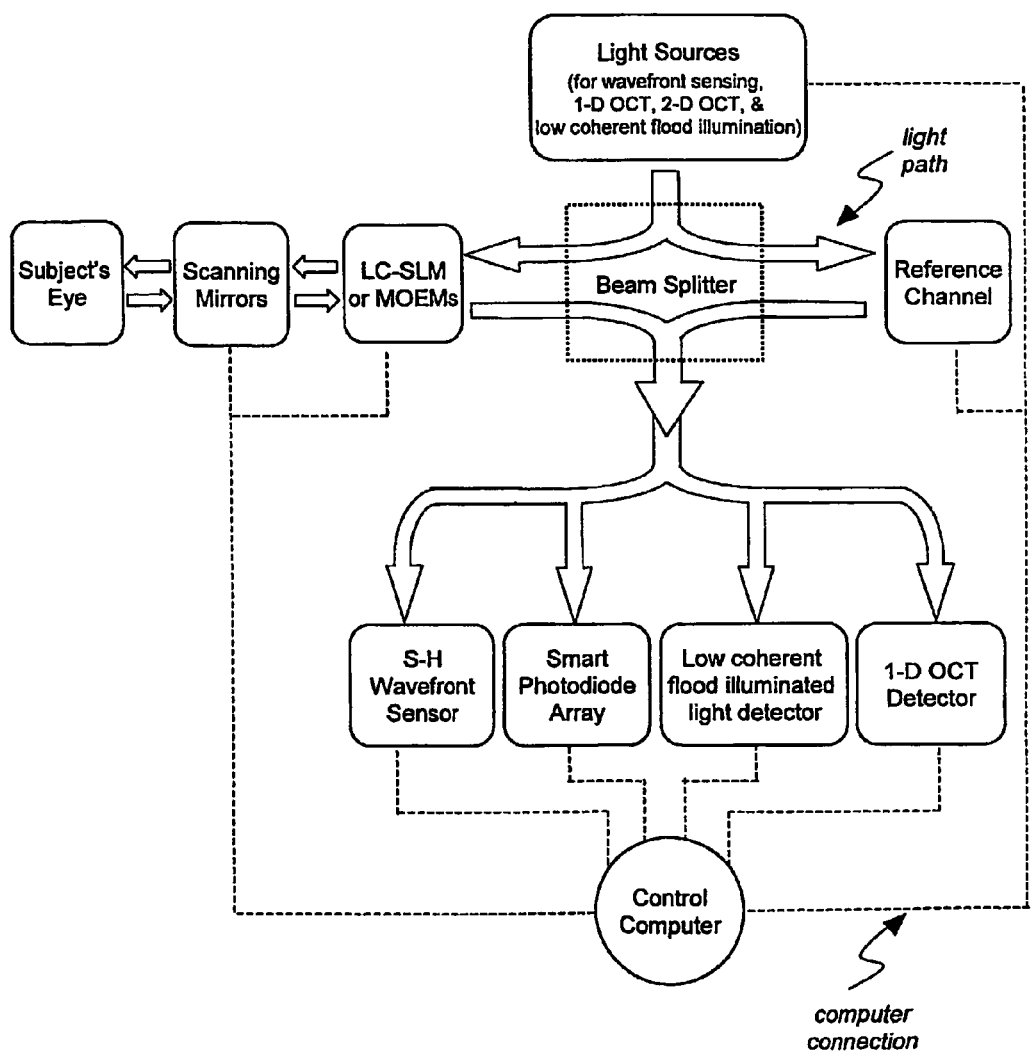
FIG. 4 depicts a flowchart representing a scanning AO-OCT apparatus according to a preferred embodiment of the invention.

In other preferred embodiments, the AO-OCT apparatus is a scanning AO-OCT camera as represented in FIG. 4, wherein the 2D-OCT subsystem consists of a 2D-OCT light source 20 that is a SLD, scanning mirrors, and a photodetector 26 and the AO subsystem consists of a Shack-Hartmann wavefront sensor 12 and a LC-SLM or MOEMs wavefront corrector 14. The scanning mirrors can be any suitable scanning mirrors and typically are raster-scanning mirrors in which the light beam is scanned using a resonant scanner/galvanometric scanner combination, which scans the light beam in both horizontal (x) and vertical (y) directions, or in a tranverse direction (i.e. either x or y) and the axial direction (z). The apparatus of this embodiment also comprises an electromechanical or electro-optical device (e.g. shutter) for blocking the reference channel, in this way permitting the system to perform as a scanning laser ophthalmoscope for focusing and aligning the coherence gate, a 1D-OCT axial scanning subsystem, and a low coherent flood illumination subsystem as described above. The apparatus of this embodiment can be realized as either a free-space or fiber-based system.

In yet another aspect of the invention, the method of optically imaging sample 50 comprises correcting aberrations associated with sample 50 by (i) illuminating sample 50 with a light beam from point light source 10 having a wavefront, (ii) detecting the wavefront of the point source light beam that is reflected from sample 50 with wavefront sensor 12 to measure wavefront distortions associated with sample 50, and (iii) adjusting wavefront corrector 14 so as to compensate for wavefront distortions that are associated with sample 50; tracking axial motion of sample 50 by (iv) generating a beam of low temporal coherence 1D-OCT light from light source 30, (v) splitting the beam of low temporal coherence 1D-OCT light to create a 1D-OCT sample light beam and a 1D-OCT reference light beam, each having an optical path length corresponding to a coherence gate position at a desired region of sample 50 to be imaged, (vi) illuminating sample 50 with the 1D-OCT sample light beam, (vii) illuminating reference mirror 24 with the 1D-OCT reference light beam, (viii) superimposing the reflected sample light beam and reflected reference light beam to obtain an interference pattern corresponding to the coherence gate position, (ix) recording a series of interference patterns corresponding to a series of coherence gate positions using 1D-OCT detector 32, (x) determining a change in axial position of sample 50 by analyzing the interference patterns recorded by 1D-OCT detector 32, and (xi) adjusting the optical path length of the reference light beam so as to axially move the coherence gate position of the sample light beam thereby compensating for the measured axial motion of sample 50; targeting a region of sample 50 to be imaged by (xii) illuminating sample 50 with a low coherent flood illumination light source 40 to focus on a region of sample 50, (xiii) detecting the low coherent flood illumination light reflected of sample 50 with a low coherent flood illumination light detector (e.g., 2D-OCT detector 26), and (xiv) optionally adjusting the focus within the sample to image at a plurality of depths in sample 50; and producing an optical image of sample 50 by (xv) generating a beam of low temporal coherence 2D-OCT light from light source 20, (xvi) splitting the second beam of low temporal coherence light to create a sample light beam and a reference light beam, each having an optical path length corresponding to a coherence gate position at a desired region of the sample to be imaged, (xvii) illuminating sample 50 with the sample light beam, (xviii) illuminating reference mirror 24 with the reference light beam, (xix) superimposing the reflected sample light beam and reflected reference light beam to obtain an interference pattern at the coherence gate position, (xx) recording the interference pattern using 2D-OCT detector 26, (xxi) generating a 2D image from the interference pattern.

The method and apparatus of the invention can be used to provide diagnostic information about the sample being imaged. For example, when the sample is an eye, the method and apparatus can be used to diagnose a retinal pathology, monitor the treatment of a retinal pathology or to locate laser burns on the retina. Preferably, the retinal pathology can be selected from the group consisting of macular degeneration, retinitis pigmentosa, glaucoma, and diabetic retinopathy. The method and apparatus also can be used to locate and assess regions of the retina to undergo surgery. For example, the AO-OCT method can be used to pinpoint a site requiring laser photocoagulation with much greater accuracy than conventional microscope methods currently in use. In another embodiment, the AO-OCT method and apparatus can be used to assess the effectiveness of a pharmaceutical drug, for example a pharmaceutical drug for treating macular degeneration, on preventing, slowing, or reversing the retinal pathology. When the sample is the lens or cornea of the eye, similar diagnostic applications are possible.

The method and apparatus of the invention also can be used in conjunction with any type of OCT technique, many of which are commonly known in the art. For example, adaptive optics can be incorporated into Polarization Sensitive OCT, which detects the polarization state of a sample reflection and can be used, for example, to determine the birefringence of a sample; Spectral OCT, in which the wavelength dependent amplitudes and phases of the reflected sample light are obtained with the help of an interferometric spectrometer; Doppler OCT, which detects offsets in the Doppler frequency due to sample movement and can be used, for example, to determine the velocity of blood cells through a blood vessel, holographic OCT, in which detection by holographic recording is intrinsically confined to reflected sample light originating at the coherence gate position as well as Phase Resolved OCT, in which phase information of the sample is recovered.

The following examples further illustrate the invention but, of course, should not be construed as in any way limiting its scope.

EXAMPLE 1

This example demonstrates a method of optical imaging that combines optical coherence tomography and adaptive optics.

A parallel OCT system based on a free-space Michelson interferometer design was constructed. The OCT system comprised a superluminescent diode having a wavelength ($\lambda$) of 679 nm, a voice coil and piezo-electric translators (Polytec PI, Auburn, Mass.) for adjusting the OPL of the reference channel, and a scientific grade 12-bit CCD array camera for detecting and recording the 2D interferograms. En-face image slices of an in vitro bovine retina were obtained using a four-step phase shift reconstruction method. The system collected four images over a 7 msec time period. Each image required a 1 msec duration followed by a 1 msec delay to allow $\lambda/8$ movement of the piezo-electric reference mirror, corresponding to a $\lambda/4$ phase delay. The dynamic range of the OCT system was measured by positioning a planar mirror in the sample channel and sweeping the reference mirror. The performance of the optical imaging system was quantified by obtaining 3-D reconstructions of a stack of microscope cover slips of known thickness and refractive index. 3-D reconstructions were also obtained of an in vitro bovine retina over a range of magnifications.

The dynamic range of the system was measured at greater than 40 dB, which is substantially higher than conventional flood-illumination and better than that of the confocal laser scanning ophthalmoscope, a competing optical slicing methodology. 3-D reconstructions of the microscope cover slips were found to be repeatable and correlated well with direct micrometer measurements. The 3-D reconstructions of an in vitro bovine retina had sufficient sensitivity to reveal clear stratification of several retinal and choroidal layers, and arrangement of individual blood vessels. FIG. 5a shows a conventional flood-illuminated image of a small patch of bovine retina (realized by blocking the reference channel) that depicts two blood vessels intersecting near the image center. A stack of 61 en face OCT reconstructions spaced 15 microns apart and covering a total depth of 915 microns were obtained of this same patch of retina From the 61 reconstructions, four cross-sectional slices were extracted and are shown in FIG. 5b. The slices reveal that the two vessels lie on top of the retina. Interestingly, an unidentified dark cylindrical structure lying immediately to the right of the main vessel is clearly observed in the OCT cross sections, yet is not visible in the conventional flood-illuminated image.

This example illustrates that the optical imaging method of the invention, which combines coherence gating and adaptive optic techniques, can provide images having both high axial and transverse resolution.

EXAMPLE 2

This example illustrates the optical imaging method of the invention comprising the use of an AO-OCT retina camera.

AO-OCT Camera Description: An AO-OCT retina camera was developed based on a free-space Michelson interferometer design. A flood-illuminated en face OCT scheme was chosen that acquired aerial images of the retina with a scientific-grade CCD camera. A major strength of this parallel approach was its insensitivity to retinal motion blur as thousands of points could be collected simultaneously. An additional advantage was its compatibility with adaptive optics. The camera consisted of four independent yet highly synchronized subsystems to perform AO, 2D low coherent flood illumination imaging, 2D en face OCT imaging, and 1D-OCT axial scanning. Each subsystem is described below.

AO Subsystem: The AO subsystem consisted of a 37 actuator Xinetics mirror and a Shack-Hartmann wavefront sensor employing a 17×17 lenslet array. Light from a 788 nm SLD enters the subject's eye through a small pupil (<1 mm in diameter) and focuses down to a spot on the retina Reflected light from the retinal spot fills the natural pupil of the eye and is distorted as it passes back through the refracting media of the eye. A two-dimensional lenslet array, placed conjugate with the eye's pupil, samples the exiting wavefront forming an array of images of the retinal spot. A CCD sensor placed in the back focal plane of the lenslets records the spots. Lateral shifts of the spots correspond to wavefront slope errors from which the aberrated wavefront of the eye is computed. Wavefront compensation is realized with the Xinetics mirror that lies in a plane conjugate to the subject's pupil and the lenslet array. The mirror surface is warped to cancel the measured aberrated wavefront. The closed-loop control operates at up to 22 wavefront measurements and corrections per second, which should be sufficient for capturing most temporal fluctuations in the wave aberrations of the human eye. Correction was over a large 6.8 mm pupil. Exposure level was less than 7 microWatts, more than 80 times below the maximum permissible exposure recommended by the American National Standards Institute for continuous illumination. Performance of the AO system was quantified by measuring the RMS of the wavefront aberrations before and after compensation of the ocular aberrations across the central 6.8 mm pupil in one subject's eye.

2-D en face Low Coherent Flood-illuminated Imaging Subsystem: The confounding effect of speckle and the limited amount of tissue information present in the micron-thin optical sections of OCT pose serious obstacles for effective focusing in retinal tissue. To circumvent these, a separate low coherent light source flood illuminated the same patch of retina as the 2-D en face OCT. The wavelengths were sufficiently similar to assure negligible chromatic error in focus between the 2-D low coherent flood illumination and 2D-OCT images. The reference channel of the OCT sub-system was physically blocked and the retinal CCD detector captured speckle-free aerial images of the retina.

2-D en face OCTImaging Subsystem: Light source for the en face interferometric system was a 10 milliwatt SLD ($\lambda$=679 nm, $\Delta\lambda$=9 nm) that flood-illuminated a 0.5 deg patch of retinal tissue. A voice coil and piezoelectric translator controlled the OPL of the reference channel and a scientific-grade 12-bit CCD array recorded 2-D retinal interferograms. En face slices of retinal tissue were obtained using a four-step phase shift reconstruction method, analogous to that employed by phase-shift interferometry. The interferograms recorded by the CCD are mathematically similar to that of conventional OCT without the heterodyning phase term. The system was capable of collecting four interferograms in less than 7 msec, each 1 msec in duration followed by a 1 msec delay to allow $\lambda/8$ movement of the piezoelectric mirror. Longer 4 msec exposures were sometimes used to assure filling the pixel well capacity of the CCD. For the latter case, the exposure level was less than 1.1 milliwatts, almost 12 times below the maximum permissible exposure recommended by the American National Standards Institute for four consecutive 4 msec pulses.

1D-OCT Axial Scanning Subsystem: The 1D-OCT system performed up to 20 A-scans per second, each traversing the full thickness of the retina, and custom software that tracked the axial position of the retina in real time. The 1D-OCT employed an 856 nm superluminescent diode (SLD) that was focused onto the retina; a voice coil stage in the reference channel for scanning the coherence gate over a 6 mm range (in air); and a New Focus photodiode and Stanford lock-in amplifier for detecting and de-modulating the heterodyned 1-D signal. Exposure level was less than 80 microWatts, more than 9 times below the maximum permissible exposure recommended by the American National Standards Institute for continuous illumination. Sensitivity of the 1D-OCT system was assessed using a model eye (stationary) as a substitute for the human eye.

1D-OCT Eye Measurements: Measurements were collected on several subjects with and without mydriatic and cycloplegic agents to determine their impact on the magnitude of retinal motion. Axial root mean square (RMS) displacement of each subject's retina was measured for each trial over periods up to 10 seconds. Microfluctuations in axial position of the stationary model eye were measured at 0.7 microns RMS over 10 second intervals and reflect the noise floor of the 1D-OCT. Axial motion was measured in several subjects with typical fluctuations between 10 and 30 microns RMS over 10 second intervals. The topical application of cycloplegic and mydriatic agents had little effect on the magnitude of the retinal movement. We attribute the retinal motion to involuntary head and eye movements rather than fundus pulsation as the latter is documented to be only a few microns peak-to-valley. The 2 seconds required for the voice coil in the reference channel to sufficiently stabilize reduced the effectiveness of the OCT system to compensate retinal motion. Nevertheless the 10 to 30 microns RMS is reasonably smaller than the thickness of the human retina (>200 microns) and suggests that meaningful optical sectioning can still occur with the AO-OCT camera.

Dynamic Range of AO-OCT System: The dynamic range of the 2-D en face OCT system was measured by positioning a planar mirror in the sample channel and sweeping the reference mirror. Performance was further validated by obtaining reconstructions of a stack of microscope cover slips of known thickness and refractive index. To initially circumvent eye motion artifacts and other complications stemming from the use of subjects, a model eye was constructed that consisted of a section of fresh bovine retina and accompanying scleral tissue, and an achromat lens (f=17 mm, dia=8 mm) and neutral density filters of 4.0 to mimic the optical properties of the eye. The entire tissue was submerged in saline solution. The OCT camera was focused on a visible blood vessel and the coherence gate was stepped through the retina in 4.5 µm steps. Ten reconstructions were obtained at each step and then averaged. Each reconstruction was obtained by applying a four step reconstruction algorithm to a sequence of four 1 msec images, which were collected in 7 msec. The dynamic range of the system was measured at greater than 36 dB, which is substantially higher than conventional flood-illumination and better than that of the confocal laser scanning ophthalmoscope, a competing optical slicing methodology. The sensitivity of the system was measured at 76 dB using the four step algorithm and 86 dB using a five step algorithm which utilized a sequence of five 1 msec images.

Reproducibility of AO-OCT Measurements: The performance of the optical imaging system was quantified by obtaining 3-D reconstructions of a stack of microscope cover slips of known thickness and refractive index. 3-D reconstructions of the microscope cover slips were found to be repeatable and correlated well with direct micrometer measurements.

AO-OCT of In Vitro Bovine and Goldfish Retinas: As a first step towards validating the en face OCT system and to avoid complications arising from human eyes (e.g., motion artifacts), through gated images were obtained on in vitro bovine and goldfish samples. Enface slices of the retina were obtained using a four-step phase shift reconstruction method, analogous to that employed by phase-shift interferometry cameras. The system is capable of collecting four images in less than 7 msec, although longer exposures typically are used to increase the signal to noise. Each of the four images was followed by a 1 msec delay to allow $\lambda/8$ movement of the piezo-electric mirror. FIG. 6a shows a cross-sectional slice (x-z) through a stack of en face (x-y) coherence gated reconstructions of an in vitro bovine retina. FIG. 6b shows a subsection of the x-z slice with the transverse and depth dimensions resized to the same linear scale. The resized image reveals blood vessels (dark patches) that are circular as would be predicted by histology.

Note the relatively sharp edges of the 54 µm diameter blood vessels. The dark region on top is saline solution, which as anticipated reflected little light; the middle gray band is believed to be the retina; the dark elliptical structures lying immediately below the retinal surface are cross sections through small blood vessels; and the bright band deeper in the tissue is suggestive of the highly reflective retinal pigment epithelium (RPE) layer and choriod. The bright band starts at 365 µm below the retinal surface. The resized image reveals blood vessels (dark patches) that are circular as would be predicted by histology. Note the relatively sharp edges of the 54 µm diameter blood vessels that is indicative of the 14 µm axial resolution. The natural appearance of the images including sharp yet curved boundaries between the saline solution, retina, and RPE as well as the circular appearance of the vessels provides strong suggestive evidence that the coherence gate is indeed stepping accurately through the tissue sample. As the CCD camera remained focused on the blood vessel for all reconstructions, spatial resolution was poor through much of the image. Yoking the focal plane to the coherence gate will remove this limitation.

Figure 7B:
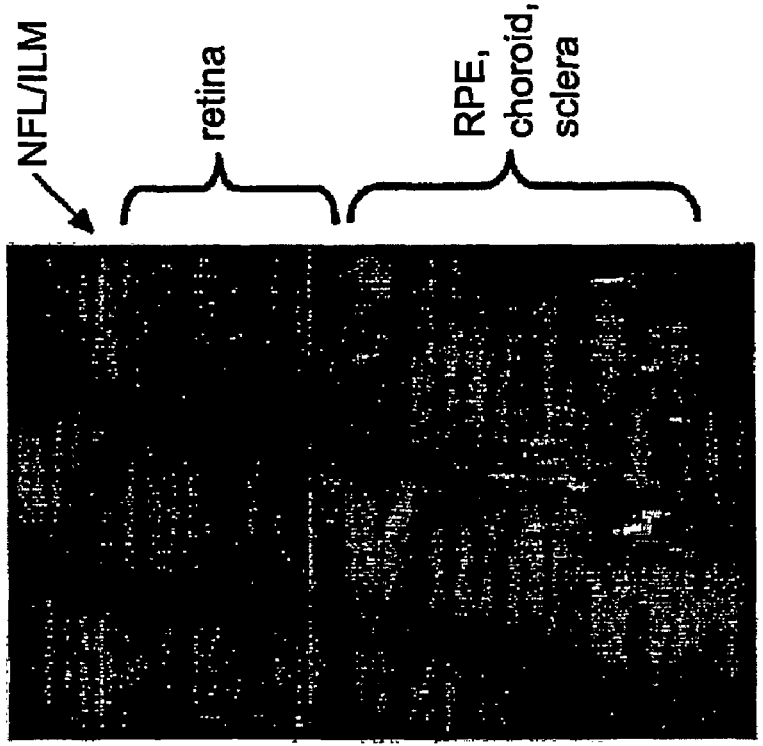
FIG. 7b depicts a cross-sectional slice (x-z) through a stack of en face (x-y) coherence gated reconstructions of an in vitro goldfish retina.
Figure 7A:
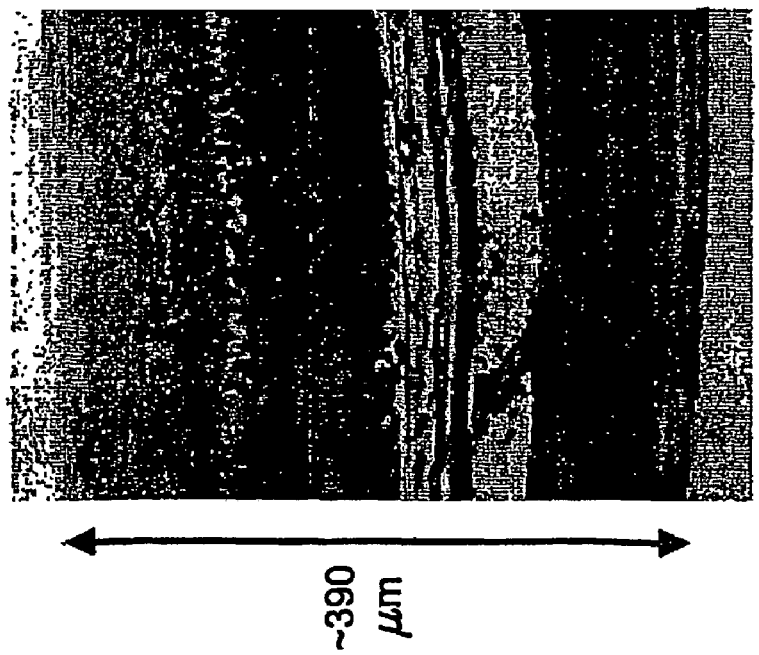
FIG. 7a depicts a histological image of an in vitro goldfish retina.

Because we had little control over the sacrifice time of the bovine eye, we next performed a similar experiment on two goldfish eyes with special attention on minimizing the time delay between sacrifice and image collection. FIG. 7b shows a cross-sectional slice (x-z) through a stack of en face (x-y) coherence gated reconstructions of an in vitro goldfish retina. FIG. 7a shows a histological sample collected on the same eye at approximately the same physical location. Note the reasonable correlation in retinal and choriodal thickness between histology and coherence gated tomographs. Features in the tomograph are reasonably well corroborated by measurements in the histology. The fresher fundus is found to have a noticeably more transparent retina.

Figure 8B:
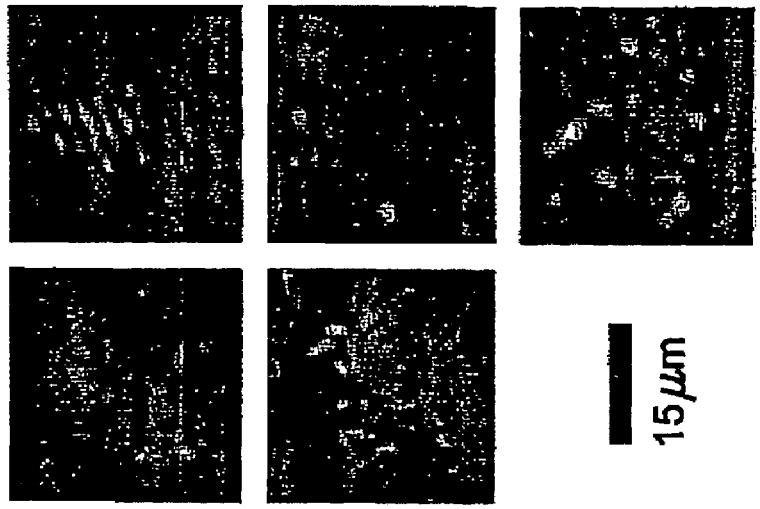
FIG. 8b depicts five individual single en face (x-y) reconstructions of a living human retina
Figure 8A:
FIG. 8a depicts a cross-sectional slice (x-z) through a stack of 41 reconstructions of a living human retina

AO-OCT on In Vivo Human Eyes: Armed with these results on in vitro eyes, we next performed through gating on one subject. The AO-OCT camera was focused on the photoreceptor layer of the eye using the conventional incoherent flood illumination light source. The coherence gate was stepped through the retina in 10 µm steps with the 1D-OCT measuring the axial retina location prior to each image collection. The AO system provided a fixed correction across a 6.8 mm pupil at the eye with retinal interferograms collected through a smaller 6 mm pupil. Wavefront aberrations were reduced from approximately 0.5 to <0.15 microns RMS. Interferograms were collected of a 0.5 deg. patch of retina at 6 deg. eccentricity (inferior). Each reconstruction was obtained from a sequence of four 4 msec images that approached one half the pixel well capacity of the retinal CCD. 42 reconstructions were collected in total. FIG. 8a shows a cross-sectional slice (x-z) through the stack of 41 reconstructions that clearly reveals bright reflections at what is likely the inner limiting membrane, retinal pigment epithelium, and choriod. Although the dynamic range in the image is less than 25 dB, the through gating results indicate this range is sufficient for capturing high spatial resolution en face images of several bright tissue layers. FIG. 8b shows five small sections of en face reconstructions obtained from different depths in the volume data. Note the variation in pattern across the five images. Although not confirmative, it is suggestive of the presence of retinal structure as the pattern of noise (i.e. speckle) should be similar in all five.

Figure 9A:
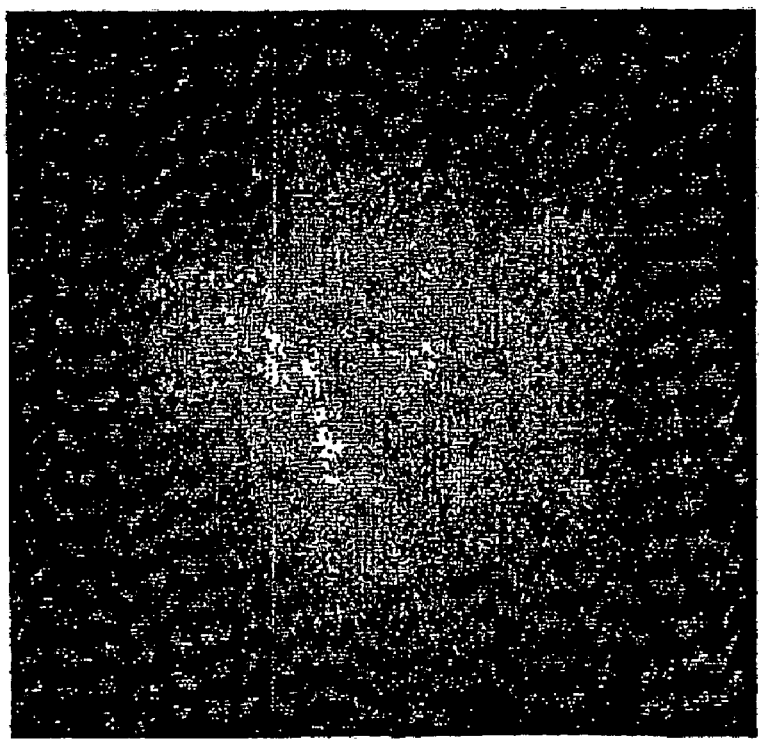
FIG. 9a depicts a low coherence flood illuminated image of the cone photoreceptor mosaic in a living human retina without adaptive optics.
Figure 9B:
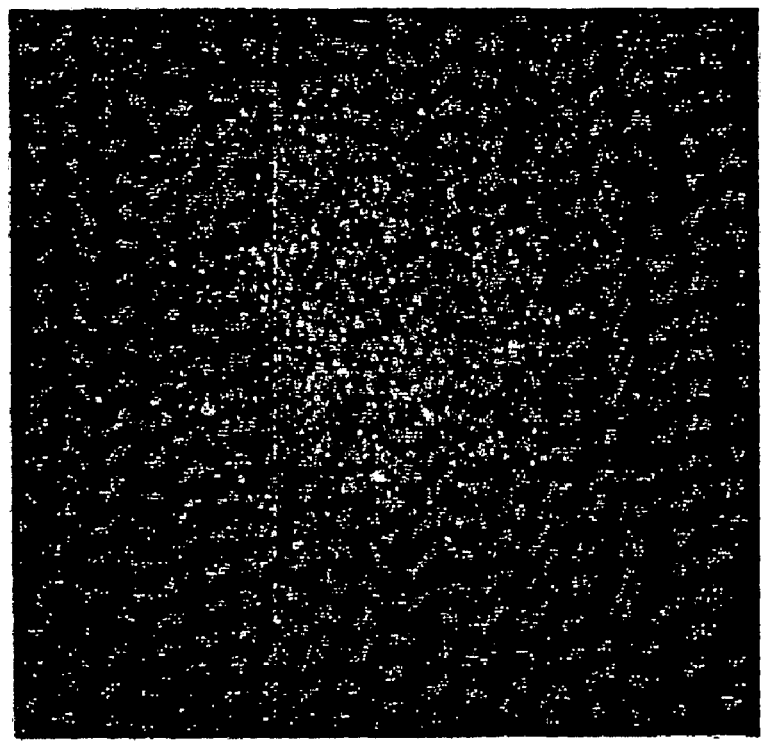
FIG. 9b depicts a flood-illuminated image of the cone photoreceptor mosaic in a living human retina with adaptive optics.

2-D en face Low Coherent Flood-illuminated Imaging with Adaptive Optics: In this example, the existing low temporal coherence light source for 2D-OCT is passed through a multi-mode fiber. This renders the light incoherent and permits high imaging rates (~8 Hz). The multi-mode fiber is a 5,000-mode fiber having a diameter of 100 µm. Low coherent flood-illuminated images of the cone mosaic at several eccentricities were captured in one subject's eye with and without adaptive compensation. The subject's eye was aligned to the retina camera using an x-y-z bite bar stage and Tropicamide 1% was administered every hour to maintain dilation of the pupil. Images were collected through a 6 mm pupil, and speckle-free illumination was provided by the incoherent light source. Retinal images were collected at continuous rates up to 8 images per second, which was found to provide easy focusing and exploration of the living retina. The AO system provided a dynamic correction at up to 22 Hz across a 6.8 mm pupil at the eye with retinal images recorded through a smaller 6 mm pupil. Wavefront aberrations were reduced from approximately 0.5 to <0.15 microns RMS. Further validation was obtained by capturing flood-illuminated images of the cone mosaic at 2.5 deg. eccentricity in the same subject with and without adaptive compensation. FIG. 9a (without AO) and FIG. 9b (with AO) show two representative images of the cone mosaic that illustrate the noticeable improvement in image clarity that can be obtained with the AO correcting additional aberrations of the eye beyond those corrected with trial lenses to achieve best focus. Short bursts of four images taken at high speeds (500 Hz) were captured in the capillary layer of the retina. The very high imaging speed coupled with adaptive optics allowed the imaging of small capillaries, individuation of single blood cells, and precise measurement of blood flow velocities in the capillaries.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of optical imaging comprising:
providing a sample to be imaged;
measuring and correcting aberrations associated with the sample using adaptive optics;
and imaging the sample by optical coherence tomography (OCT);
wherein the aberrations associated with the sample are measured and corrected by (i) illuminating the sample with a point source light beam having a wavefront, (ii) detecting the wavefront of the point source light beam that is reflected from the sample with a wavefront sensor to measure wavefront distortions of the sample, and (iii) adjusting a wavefront corrector so as to compensate for the wavefront distortions that are associated with the sample;
wherein the sample is imaged by (iv) generating a beam of low temporal coherence two-dimensional (2D) OCT light from a light source, (v) splitting the beam of low temporal coherence light to create a sample light beam and a reference light beam, each having an optical path length corresponding to a coherence gate position at a desired region of the sample to be imaged, (vi) illuminating the sample with the sample light beam, (vii) illuminating a reference mirror with the reference light beam, (viii) superimposing the reflected sample light beam and reflected reference light beam to obtain an interference pattern corresponding to the coherence gate position, (ix) recording the interference pattern using a detector, (x) generating a two-dimensional image of the sample from the interference pattern; and
wherein steps (i)-(iii) are carried out concurrently with steps (iv)-(ix).

2. A method of optical imaging comprising:
providing a sample to be imaged;
measuring and correcting aberrations associated with the sample using adaptive optics;
and imaging the sample by optical coherence tomography (OCT);
wherein the aberrations associated with the sample are measured and corrected by (i) illuminating the sample with a point source light beam having a wavefront, (ii) detecting the wavefront of the point source light beam that is reflected from the sample with a wavefront sensor to measure wavefront distortions of the sample, and (iii) adjusting a wavefront corrector so as to compensate for the wavefront distortions that are associated with the sample;
wherein the sample is imaged by (iv) generating a beam of low temporal coherence two-dimensional (2D) OCT light from a light source, (v) splitting the beam of low temporal coherence light to create a sample light beam and a reference light beam, each having an optical path length corresponding to a coherence gate position at a desired region of the sample to be imaged, (vi) illuminating the sample with the sample light beam, (vii) illuminating a reference mirror with the reference light beam, (viii) superimposing the reflected sample light beam and reflected reference light beam to obtain an interference pattern corresponding to the coherence gate position, (ix) recording the interference pattern using a detector, (x) generating a two-dimensional image of the sample from the interference pattern; and
wherein the method further comprises tracking and compensating for axial motion of the sample by:
generating a beam of low temporal coherence 1D-OCT light from a light source,
splitting the beam of low temporal coherence 1D-OCT light to create a 1DOCT sample light beam and a 1D-OCT reference light beam, each having an optical path-length corresponding to a coherence gate position at a desired region of the sample to be imaged,
illuminating the sample with the 1D-OCT sample light beam,
illuminating the reference mirror with the 1D-OCT reference light beam,
superimposing the reflected sample light beam and reflected reference light beam to obtain an interference pattern corresponding to the coherence gate position,
recording a series of interference patterns corresponding to a series of coherence gate positions using a 1D-OCT detector,
determining a change in axial position of the sample by analyzing the interference patterns recorded by the 1D-OCT detector,
and adjusting the optical path length of the reference light beam so as to axially move the coherence gate position of the sample light beam thereby compensating for the measured axial motion of the sample.

3. The method of claim 2, wherein the method of tracking and compensating for axial motion of the sample is completed prior to step (ix).

4. The method of claim 2, wherein the method of tracking and compensating for axial motion of the sample is carried out prior to and concurrently with steps (iv)-(ix).

5. The method of claim 2, wherein the sample is an eye and the change in axial position is analyzed using a portion of the 1D-OCT low temporal coherence light that is reflected off of a region of the eye selected from the group consisting of a choriod layer, a retinal pigment epithelium layer, and a front layer of a retina.

6. An optical imaging apparatus comprising:
an adaptive optics (AO) subsystem;
a two-dimensional optical coherence tomography (2D-OCT) subsystem; and
a one-dimensional optical coherence tomography (1D-OCT) axial scanning subsystem comprising a low temporal coherence 1D-OCT light source and a 1D-OCT detector.

7. An optical imaging apparatus comprising:
an adaptive optics (AO) subsystem;
a two-dimensional optical coherence tomography (2D-OCT) subsystem; and
a low coherence flood illumination light source;
wherein the low coherence flood illumination light source is selected from the group consisting of a laser diode, a femtosecond laser, a mode-locked solid state laser, a dye laser, a superluminescent diode, and a light emitting diode; and
wherein the low coherence flood illumination light source is coupled to a multi-mode fiber.

8. A method of optically imaging a sample comprising:
correcting aberrations associated with the sample by:
(i) illuminating the sample with a point source light beam having a wavefront,
(ii) detecting the wavefront of the point source light beam that is reflected from the sample with a wavefront sensor to measure wavefront distortions of the sample, and (iii) adjusting a wavefront corrector so as to compensate for the wavefront distortions that are associated with the sample; tracking axial motion of the sample by:

(iv) generating a beam of low temporal coherence 1D-OCT light from a light source, (v) splitting the beam of low temporal coherence 1D-OCT light to create a 1D-OCT sample light beam and a 1D-OCT reference light beam, each having an optical path length corresponding to a coherence gate position at a desired region of the sample to be imaged, (vi) illuminating the sample with the 1D-OCT sample light beam, (vii) illuminating the reference mirror with the 1D-OCT reference light beam, (viii) superimposing the reflected sample light beam and reflected reference light beam to obtain an interference pattern corresponding to the coherence gate position, (ix) recording a series of interference patterns corresponding to a series of coherence gate positions using a 1D-OCT detector, (x) determining a change in axial position of the sample by analyzing the interference patterns recorded by the 1D-OCT detector, and (xi) adjusting the optical path length of the reference light beam so as to axially move the coherence gate position of the Sample light beam thereby compensating for the measured axial motion of the sample; targeting a region of the sample to be imaged by:

(xii) illuminating the sample with a low coherent flood illumination light source to focus on a region of the sample, (xiii) detecting the low coherent flood illumination light that is reflected from the sample with a low coherent flood illumination light detector, and (xiv) optionally adjusting the focus within the sample to image at a plurality of depths in the sample; and producing an optical image of the sample by:

(xv) generating a beam of low temporal coherence 2D-OCT light from a light source, (xvi) splitting the beam of low temporal coherence light to create a sample light beam and a reference light beam, each having an optical path length corresponding to a coherence gate position at a desired region of the sample to be imaged, (xvii) illuminating the sample with the sample light beam, (xviii) illuminating a reference minor with the reference light beam, (xix) superimposing the reflected sample light beam and reflected reference light beam to obtain an interference pattern corresponding to the coherence gate position, (xx) recording the interference pattern using a 2D-OCT detector, and (xxi) generating a two-dimensional image of the sample from the interference pattern.

9. An optical imaging apparatus comprising (a) a point light source for adaptive optics, (b) a Shack-Hartmann wavefront sensor, (c) a wavefront corrector, (d) a low temporal coherent superluminescent diode 2D-OCT light source, (e) a beam splitter, (f) a reference mirror, (g) a means of modulating an optical path length of a reference beam, (h) a 2D-OCT CCD detector, (i) a 1D-OCT low temporal coherence superluminescent diode light source, (i) a 113-OCT detector, and (k) a low coherent flood illumination light source coupled to a multi-mode fiber.

10. A method for optically imaging a sample of retinal or fundus tissue in an eve, the method comprising:

(a) providing an optical imaging system comprising an adaptive optical element;

(b) measuring wavefront aberrations in the eye;

(c) controlling the adaptive optical element to correct the wavefront aberrations measured in step (b);

(d) performing a first optical coherence tomography operation on the sample to determine a distance from the sample to the optical imaging system;

(e) adjusting the optical imaging system to compensate for the distance determined in step (d); and (f) performing a second optical coherence tomography operation on the sample to image the sample;

wherein the second optical coherence tomography operation is a two-dimensional optical coherence tomography operation; and wherein the first optical coherence tomography operation is a one-dimensional optical coherence tomography operation.

11. A method for optically imaging a sample of retinal or fundus tissue in an eye, the method comprising:

(a) providing an optical imaging system comprising an adaptive optical element;

(b) measuring wavefront aberrations in the eye;

(c) controlling the adaptive optical element to correct the wavefront aberrations measured in step (b);

(d) illuminating the sample with low coherent flood illumination light;

(e) detecting the low coherent flood illumination light reflected from the sample; and (f) adjusting a focus of the optical imaging system in accordance with the low coherent flood illumination light detected in step (e); and (g) performing an optical coherence tomography operation on the sample to image the sample;

wherein a single detector in the optical imaging system is used to perform steps (e) and (g); and wherein step (d) is performed with a light source coupled to a multimode optical fiber.

12. The method of claim 11, wherein the light source comprises a laser diode.

13. The method of claim 11, wherein the light source comprises a superluminescent diode.

14. A method for optically imaging a sample of retinal or fundus tissue in an eye, the method comprising:

(a) providing an optical imaging system comprising an adaptive optical element;

(b) measuring wavefront aberrations in the eye;

(c) controlling the adaptive optical element to correct the wavefront aberrations measured in step (b);

(d) illuminating the sample with low coherent flood illumination light by using a light source coupled to a multimode optical fiber;

(e) detecting the low coherent flood illumination light reflected from the sample; and (f) adjusting a focus of the optical imaging system in accordance with the low coherent flood illumination light detected in step (e); and (g) performing an optical coherence tomography operation on the sample to image the sample.

15. The method of claim 14, wherein the light source comprises a laser diode.

16. The method of claim 14, wherein the light source comprises a superluminescent diode.

17. A method for optically imaging a sample of retinal or fundus tissue in an eye, the method comprising:
(a) providing an optical imaging system comprising an adaptive optical element;
(b) measuring wavefront aberrations in the eye;
(c) controlling the adaptive optical element to correct the wavefront aberrations measured in step (b); and
(d) performing an optical coherence tomography operation on the sample to image the sample, wherein step (d) is performed using an active pixel array;
wherein step (d) comprises beat frequency detection.

* * * * *